United States Patent
Jian et al.

(10) Patent No.: US 10,610,166 B2
(45) Date of Patent: Apr. 7, 2020

(54) DETERMINATION OF A HEMODYNAMIC PARAMETER

(71) Applicant: Edwards Lifesciences Corporation, Irvine, CA (US)

(72) Inventors: Zhongping Jian, Irvine, CA (US); Jacobus J. G. M. Settels, De Hoef (NL); Feras Al Hatib, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 953 days.

(21) Appl. No.: 14/770,409

(22) PCT Filed: Jul. 8, 2014

(86) PCT No.: PCT/US2014/045701
§ 371 (c)(1),
(2) Date: Aug. 25, 2015

(87) PCT Pub. No.: WO2015/006295
PCT Pub. Date: Jan. 15, 2015

(65) Prior Publication Data
US 2016/0038097 A1    Feb. 11, 2016

Related U.S. Application Data

(60) Provisional application No. 61/843,722, filed on Jul. 8, 2013.

(51) Int. Cl.
*A61B 5/00* (2006.01)
*A61B 5/021* (2006.01)
(Continued)

(52) U.S. Cl.
CPC .......... *A61B 5/7278* (2013.01); *A61B 5/0205* (2013.01); *A61B 5/029* (2013.01);
(Continued)

(58) Field of Classification Search
None
See application file for complete search history.

(56) References Cited

U.S. PATENT DOCUMENTS 7,422,562 B2 *  9/2008  Hatib .................. A61B 5/02
                                                           600/485
2002/0062086 A1  5/2002  Miele et al.
(Continued)

FOREIGN PATENT DOCUMENTS

| JP | 2013-519410 | 5/2013 |
|---|---|---|
| KR | 10-0954817 | 4/2010 |
| WO | 2005055825 A1 | 6/2005 |

OTHER PUBLICATIONS

Int'l. Search Report for PCT/US2014/045701, dated Oct. 27, 2014.
(Continued)

*Primary Examiner* — Jacqueline Cheng
*Assistant Examiner* — Tho Q Tran
(74) *Attorney, Agent, or Firm* — Rick Nelson; Kinney & Lange, P.A.

(57) ABSTRACT

Embodiments of the disclosure are directed to methods, apparatuses, and computer program products for determining a hemodynamic parameter. An exemplary method comprises: receiving data associated with at least one heart beat; calculating a first standard deviation for at least a portion of the data; interpolating a second standard deviation for at least a second portion of the data; and determining the hemodynamic parameter based on the first standard deviation and the second standard deviation.

20 Claims, 7 Drawing Sheets

(51) Int. Cl.
*A61B 5/0295* (2006.01)
*G16H 50/20* (2018.01)
*A61B 5/029* (2006.01)
*A61B 5/0205* (2006.01)
*A61B 5/026* (2006.01)
*A61B 5/0215* (2006.01)
*A61B 5/024* (2006.01)

(52) U.S. Cl.
CPC .......... *A61B 5/0215* (2013.01); *A61B 5/0261* (2013.01); *A61B 5/0295* (2013.01); *A61B 5/02108* (2013.01); *A61B 5/02416* (2013.01); *A61B 5/7203* (2013.01); *A61B 5/7217* (2013.01); *A61B 5/7275* (2013.01); *G16H 50/20* (2018.01)

(56) References Cited

U.S. PATENT DOCUMENTS

| | | |
|---|---|---|
| 2004/0077953 A1 | 4/2004 | Turcott |
| 2005/0124904 A1 | 6/2005 | Roteliuk |
| 2008/0033305 A1 | 2/2008 | Hatib et al. |
| 2009/0018422 A1 | 1/2009 | Banet et al. |
| 2011/0022323 A1* | 1/2011 | Yundt-Pacheco ...... G16H 10/40 702/19 |
| 2011/0105858 A1 | 5/2011 | Cho et al. |
| 2011/0319724 A1 | 12/2011 | Cox |
| 2013/0053664 A1* | 2/2013 | Jian ...................... A61B 5/0205 600/324 |

OTHER PUBLICATIONS

Extended European Search Report issued in Application No. EP16202415.2, completed Apr. 18, 2017.

Frazier J et al: "Getting ml/beat from mmHg Arterial Pressure-based Cardiac Output The Edwards Flortrac Algorithm", Internet Citation, Jan. 1, 2012, pp. 1-4; Retrieved from the internet: URL:http://www.edwards.com/products/mininvasive/Pages/flotracalgorithmpdf.aspx.

Supplementary European Search Report issued in EP14822728, Completed Jan. 18, 2017.

* cited by examiner

DETERMINATION OF A HEMODYNAMIC PARAMETER

CROSS-REFERENCE TO RELATED APPLICATIONS

This application claims priority to U.S. Provisional Patent Application Ser. No. 61/843,722, filed Jul. 8, 2013, entitled "A Method For The Calculation Of Stroke Volume Variation," the entirety which is incorporated herein by reference.

FIELD OF TECHNOLOGY

This disclosure is related to the field of patient hemodynamic monitoring and digital signal processing. This disclosure specifically relates to a method of calculating real-time hemodynamic parameters.

BACKGROUND

Indicators such as stroke volume (SV), cardiac output (CO), end-diastolic volume, ejection fraction, stroke volume variation (SVV), pulse pressure variation (PPV), systolic pressure variations (SPV), and plethysmographic variability index (PVI), among others, are important not only for diagnosis of disease, but also for "real-time" monitoring of preload dependence, fluid responsiveness, or volume responsiveness condition of both human and animal subjects. Few hospitals are therefore without some form of equipment to monitor one or more of these cardiac parameters. Many techniques, including invasive techniques, non-invasive techniques, and combinations thereof, are in use and even more have been proposed in the literature. References that disclose determination of hemodynamic parameters include WO02011094487 (Jian et al., filed 28 Jan. 2011) and WO 2009023713 (Derderian et al., filed 13 Aug. 2008).

One way to obtain a hemodynamic parameter is to mount a flow-measuring device on a catheter, and position the device in or near the subject's heart. Some such devices inject either a bolus of material or energy (usually heat) at an upstream position, such as in the right atrium, and determine flow based on the characteristics of the injected material or energy at a downstream position, such as in the pulmonary artery. Patents that disclose implementations of such invasive techniques (in particular, thermodilution) include: U.S. Pat. No. 4,236,527 (Newbower et al., 2 Dec. 1980); U.S. Pat. No. 4,507,974 (Yelderman, 2 Apr. 1985); U.S. Pat. No. 5,146,414 (McKown, et al., 8 Sep. 1992); and U.S. Pat. No. 5,687,733 (McKown, et al., 18 Nov. 1997). Other invasive devices are based on the known Fick technique, according to which a hemodynamic parameter is calculated as a function of oxygenation of arterial and mixed venous blood. Doppler techniques, using invasive as well as non-invasive transducers, have also been used to obtain flow rate data that can then be used to calculate a hemodynamic parameter.

One blood characteristic that can be obtained with minimal or no invasion is blood pressure. In addition to causing minimal patient trauma, blood pressure measurement technology has the added benefit of being accurate and continuous. Many systems rely on the pulse contour method (PCM), which calculates an estimate of one or more hemodynamic parameters of interest from characteristics of a blood pressure waveform. In the PCM, "Windkessel" parameters, such as characteristic impedance of the aorta, compliance, and total peripheral resistance, are often used to construct a linear or non-linear hemodynamic model of the aorta. In essence, blood flow is analogized to a flow of electrical current in a circuit in which an impedance is in series with a parallel-connected resistance and capacitance (compliance). The three required parameters of the model are usually determined either empirically, through a complex calibration process, or from compiled "anthropometric" data, i.e., data about the age, sex, height, weight, and/or other parameters of other patients or test subjects. U.S. Pat. No. 5,400,793 (Wesseling, 28 Mar. 1995) and U.S. Pat. No. 5,535,753 (Petrucelli et al., 16 Jul. 1996) disclose systems that rely on a Windkessel circuit model to determine a hemodynamic parameter. PCM-based systems can monitor hemodynamic parameters using blood pressure measurements taken using a variety of measurement apparatus, such as a finger cuff, and can do so more or less continuously. Many improvements, with varying degrees of complexity, have been proposed for improving the accuracy of the basic PCM model. The present disclosure offers an improvement over the PCM model or any other models discussed in this section.

Yet more advanced methods for calculating hemodynamic parameters are described, for example, in U.S. Pat. Nos. 7,967,757, and 8,721,556, in PCT patent application publication numbers WO2009/023713 and WO2011/094487, and in PCT International Patent Application Serial No. US2014/045538, the full contents of each of which are hereby incorporated by reference in their entireties.

BRIEF SUMMARY

In some embodiments, a method for determining a hemodynamic parameter is provided. The method comprises: receiving data associated with at least one heart beat; calculating a first standard deviation for at least a portion of the data; interpolating a second standard deviation for at least a second portion of the data; and determining, using a computing device processor, the hemodynamic parameter based on the first standard deviation and the second standard deviation.

In some embodiments, the hemodynamic parameter comprises a stroke volume variation (SVV), and the data comprises blood pressure data.

In some embodiments, the hemodynamic parameter comprises a pulse pressure variation (PPV), and the data comprises pulse pressure data.

In some embodiments, the hemodynamic parameter comprises a systolic pressure variation (SPV), and the data comprises systolic pressure data.

In some embodiments, the hemodynamic parameter comprises a plethysmographic variability index (PVI), and the data comprises pulse oximeter waveform data.

In some embodiments, the method further comprises determining, using a computing device processor, a polynomial function that fits the first standard deviation, the polynomial function being associated with at least one polynomial coefficient.

In some embodiments, the polynomial function is based on a least-squares function.

In some embodiments, receiving data comprises measuring at least one arterial blood pressure waveform and identifying the at least one heart beat.

In some embodiments, the method further comprises subtracting the second standard deviation from the first standard deviation.

In some embodiments, determining the hemodynamic parameter further comprises determining the hemodynamic parameter based on a constant, a standard deviation of the second standard deviation, and a mean of the first standard deviation.

In some embodiments, determining the hemodynamic parameter further comprises determining the hemodynamic parameter based on multiplying the constant and the standard deviation of the second standard deviation to produce a first computation, and dividing the first computation by the mean of the first standard deviation.

In some embodiments, the polynomial function is a first order polynomial function.

In some embodiments, the polynomial function is an $n^{th}$ order polynomial function.

In some embodiments, an apparatus is provided for determining a hemodynamic parameter. The apparatus comprises a communication interface; a memory; a processor; and a module stored in the memory, executable by the processor, and configured to: receive data associated with at least one heart beat; calculate a first standard deviation for at least a portion of the data; interpolate a second standard deviation for at least a second portion of the data; and determine the hemodynamic parameter based on the first standard deviation and the second standard deviation.

In some embodiments, the apparatus further comprises a kit comprising at least one of a catheter and a pressure sensor associated with the catheter.

In some embodiments, the apparatus further comprises at least one of a signal filter or an analog-to-digital converter.

In some embodiments, a computer program product is provided for determining a hemodynamic parameter. The computer program product comprises a non-transitory computer-readable medium comprising a set of codes for causing a computer to: receive data associated with at least one heart beat; calculate a first standard deviation for at least a portion of the data; interpolate a second standard deviation for at least a second portion of the data; and determine the hemodynamic parameter based on the first standard deviation and the second standard deviation.

In some embodiments, an apparatus is provided for determining a hemodynamic parameter. The apparatus comprises means for receiving data associated with at least one heart beat; means for calculating a first standard deviation for at least a portion of the data; means for interpolating a second standard deviation for at least a second portion of the data; and means for determining the hemodynamic parameter based on the first standard deviation and the second standard deviation.

In some embodiments, a method is provided for determining a hemodynamic parameter. The method comprises: receiving data associated with at least one heart beat; calculating a first standard deviation for at least a portion of the data; using a Fourier transform and filtering scheme to remove at least a second portion of the data; using an inverse Fourier transform to obtain a second standard deviation for at least a second portion of the data; and determining, using a computing device processor, the hemodynamic parameter based on the first standard deviation and the second standard deviation. Apparatus and computer program product may also be provided based on this method.

In some embodiments, another method is provided for determining a hemodynamic parameter. The method comprises: receiving a first portion of data associated with at least one heart beat; interpolating a second portion of the data based on the first portion of the data; calculating at least one standard deviation for at least one of the first portion of the data or the second portion of the data; and determining, using a computing device processor, the hemodynamic parameter based on the at least one standard deviation. In some embodiments, the hemodynamic parameter comprises at least one of SVV, PPV, SPV, or PVI. Apparatus and computer program product may also be provided based on this method.

BRIEF DESCRIPTION OF THE DRAWINGS

Having thus described embodiments of the disclosure in general terms, reference will now be made to the accompanying drawings, where:

DETAILED DESCRIPTION

Embodiments of the present disclosure now may be described more fully hereinafter with reference to the accompanying drawings, in which some, but not all, embodiments of the disclosure are shown. Indeed, the disclosure may be embodied in many different forms and should not be construed as limited to the embodiments set forth herein; rather, these embodiments are provided so that this disclosure may satisfy applicable legal requirements. Like numbers refer to like elements throughout.

Embodiments of the disclosure are directed to apparatuses, methods and computer program products for determining or calculating a hemodynamic parameter. This disclosure provides a new method to calculate hemodynamic parameters such as stroke volume variation (SVV), pulse pressure variation (PPV), systolic pressure variation (SPV), and plethysmographic variability index (PVI) based on blood pressure waveforms. In today's patient hemodynamic monitoring, blood pressure is routinely monitored and many parameters that are of great clinical use, such as cardiac output, stroke volume, and stroke volume variation can be derived from blood pressure waveforms and displayed by monitors. Accurately calculating those parameters is of great importance because accurate calculations can help clinicians know more about patients and make more informed decisions in treating patients.

Exemplary methods of the present disclosure are directed to determining SVV. However, these methods or variations of these methods may be used to determine other hemodynamic parameters, including, but not limited to, SPV, PPV, or PVI. A method for calculating SVV, which is induced by mechanical ventilation, predicts fluid responsiveness with high sensitivity and specificity. As a result, it is often used by clinicians as a guide for fluid optimization. The SVV may be calculated using the formula: SVV=constant×std (std_bp)/mean(std_bp), where constant is a constant parameter, std is the standard deviation, std_bp is an array of the standard deviation of each beat in a 20 second window, and mean is the average value (e.g., average value of std_bp). Constant is an empirically determined scaling constant, which can be chosen largely for convenience and as appropriate for display to a user of a system embodying and performing the method. A suitable scaling constant might be 2.7, for example. Regardless of the number of respiratory cycles included in the computation interval; normal experimental methods may be used to determine a suitable scaling constant in any given implementation of the invention. This method of calculation or determination of the SVV may be referred to as the first method. The first method does reasonably well in predicting fluid responsiveness. The issue of this method, however, is that it does not completely distinguish the variation of stroke volume due to the mechanical ventilation from variation due to other causes. As a result, the first method may not predict fluid responsiveness with high accuracy (e.g., accuracy equal to or greater than a threshold accuracy).

Figure 1:
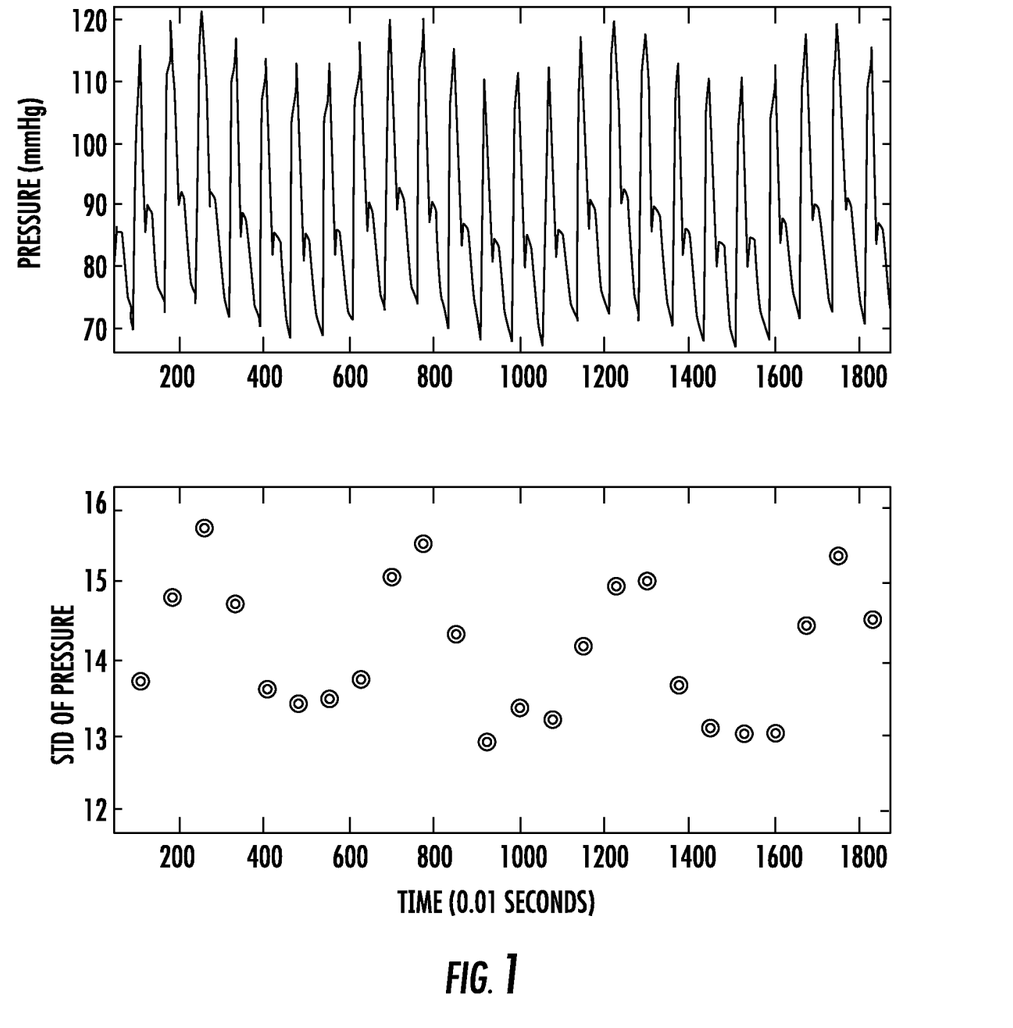
FIG. 1 shows an example of radial artery pressure before a bolus vasopressor of phenylephrine is given to patients.

FIG. 1 shows an example of radial artery pressure before a bolus vasopressor of phenylephrine is given to patients. The top plot shows the pressure and the bottom plot shows the standard deviation of blood pressure in each beat. The respiration-induced variation of stroke volume can be clearly observed in both plots of FIG. 1.

Figure 2:
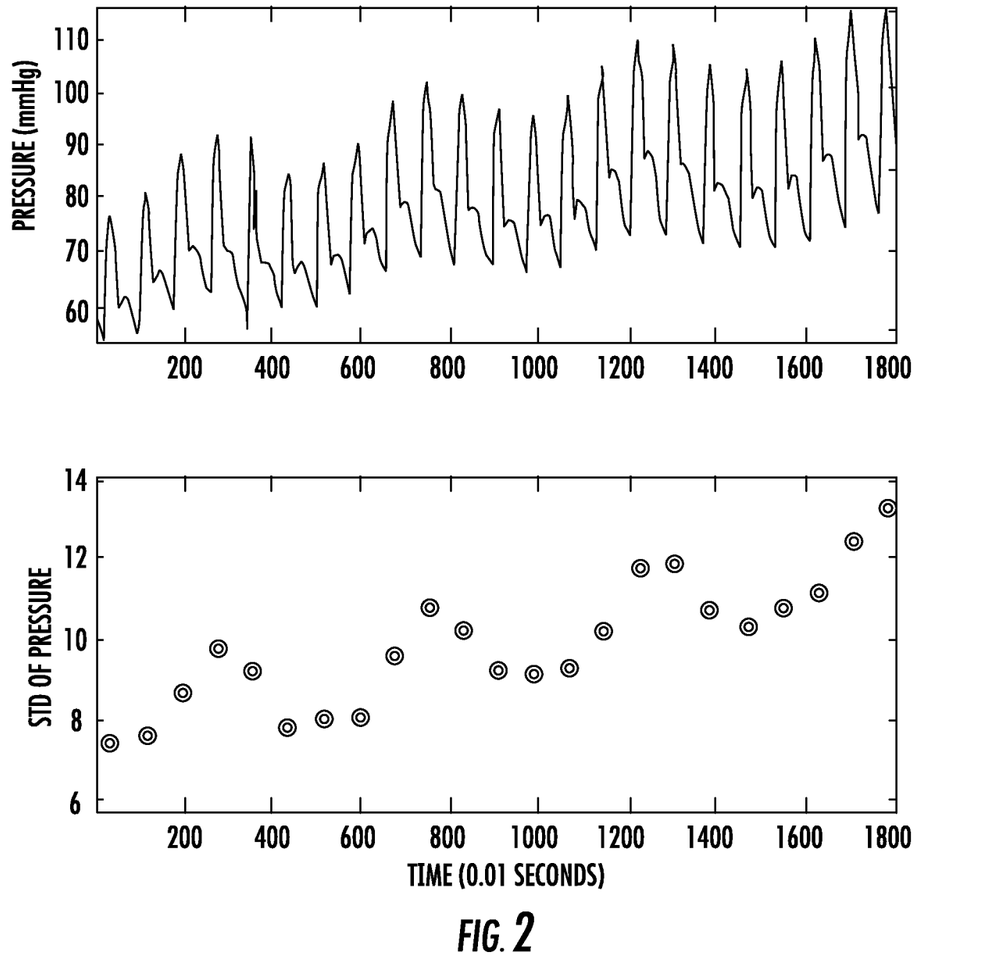
FIG. 2 shows an example of radial artery pressure after a bolus vasopressor of phenylephrine is given to patients.

FIG. 2 shows an example of radial artery pressure after a bolus vasopressor of phenylephrine is given to patients. The top plot shows the pressure and the bottom plot shows the standard deviation of blood pressure in each beat. The respiration-induced variation of stroke volume can be observed, but in addition to that, it comes with a significant change of stroke volume induced by the bolus phenylephrine.

The present disclosure is directed to a second method to determine a hemodynamic parameter such as SVV. This method removes many of the variations of stroke volume due to other sources from the determination, thus improving the sensitivity and specificity of the SVV's or any other hemodynamic parameter's ability in predicting fluid responsiveness.

Figure 5:
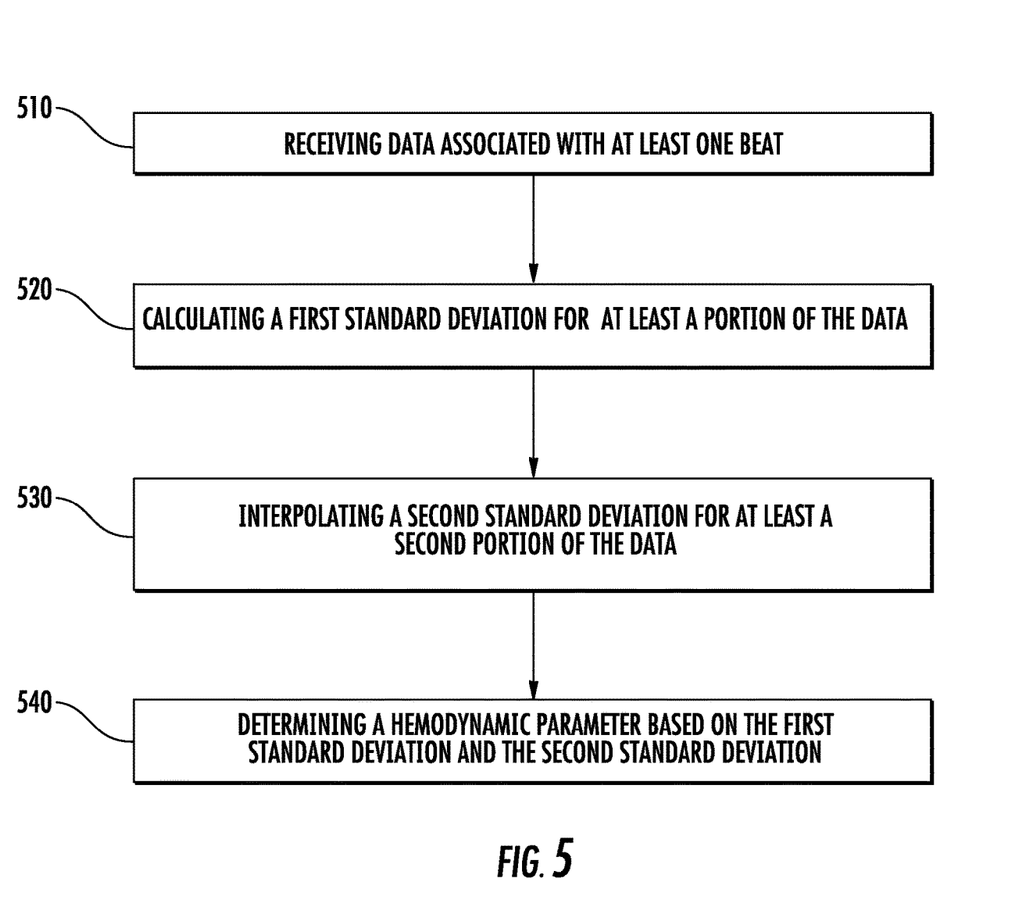
FIG. 5 shows an exemplary method for determining a hemodynamic parameter.

FIG. 5 presents an exemplary process flow or method for determining a hemodynamic parameter. This is the second method described previously. The second method is different from the first method primarily due to an interpolation step (see block 530). At block 510, the process flow comprises receiving data associated with at least one heart beat. Receiving data associated with at least one heart beat may comprise measuring a waveform and identifying at least one heart beat using a digital signal processing algorithm. In some embodiments, receiving data comprises measuring at least one arterial blood pressure waveform and identifying at least one heart beat. As indicated previously, the data may comprise a blood pressure waveform. The blood pressure waveform corresponds to a signal, for example, from an arterial blood pressure, or any signal proportional to, or derived from the arterial pressure signal such as a pulse-oximetry signal, a Doppler ultrasound signal or a bioimpedance signal. At block 520, the process flow comprises calculating a first standard deviation for at least a portion (or first portion) of the data.

The process flow further comprises determining a polynomial function that fits the first standard deviation, wherein the polynomial function (e.g., $1^{st}$ order, $2^{nd}$ order, $n^{th}$ order, or any combination thereof) is associated with at least one polynomial coefficient. The polynomial function may be based on a least-squares function. At block 530, the process flow comprises interpolating a second standard deviation for at least a second portion of the data (different from the first portion of the data). The interpolation may be performed based on the polynomial function. In some embodiments, the process flow further comprises subtracting the second standard deviation from the first standard deviation.

At block 540, the process flow comprises determining a hemodynamic parameter (e.g., associated with a non-respiration effect) based on the first standard deviation and the second standard deviation. In some embodiments, the determining of the hemodynamic parameter is further configured to determine the hemodynamic parameter based on multiplying the constant and the standard deviation of the second standard deviation to produce a first computation, and dividing the first computation by the mean of the first standard deviation. Constant is again an empirically determined or selected scaling constant. In some embodiments, the operation of determining a polynomial function and the operation depicted at 540 can be replaced with using a Fourier transform and filtering scheme (e.g., high-pass filtering scheme) to remove at least a second portion of the data, and then using an inverse Fourier transform to obtain the second standard deviation for at least a second portion of the data. As used herein, "first" standard deviation and "second" standard deviation are not used to indicate orders of standard deviation; instead, they are used to indicate a first standard deviation calculation and a second standard deviation calculation. Both the first standard deviation calculation and the second standard deviation calculation may be associated with any order of standard deviation.

The received data (as indicated in block 510) of the second method changes depending on the hemodynamic parameter that is to be determined. When determining SVV, for example, blood pressure data (comprising a blood pressure waveform) is received at block 510. At block 520, the process flow comprises calculating a first standard deviation for at least a portion (or first portion) of the blood pressure data. At block 530, the process flow comprises interpolating a second standard deviation for at least a second portion of the blood pressure data (different from the first portion of the blood pressure data). At block 540, the process flow comprises determining the SVV based on the first standard deviation and the second standard deviation.

When determining SPV, systolic pressure data (comprising a systolic pressure waveform) is received at block 510. At block 520, the process flow comprises calculating a first standard deviation for at least a portion (or first portion) of the systolic pressure data. At block 530, the process flow comprises interpolating a second standard deviation for at least a second portion of the systolic pressure data (different from the first portion of the systolic pressure data). At block 540, the process flow comprises determining the SPV based on the first standard deviation and the second standard deviation.

When determining PPV, pulse pressure data (comprising a pulse pressure waveform) is received at block 510. At block 520, the process flow comprises calculating a first standard deviation for at least a portion (or first portion) of the pulse pressure data. At block 530, the process flow comprises interpolating a second standard deviation for at least a second portion of the pulse pressure data (different from the first portion of the pulse pressure data). At block 540, the process flow comprises determining the PPV based on the first standard deviation and the second standard deviation.

When determining PVI, pulse oximeter waveform data (comprising a pulse oximeter waveform) is received at block 510. At block 520, the process flow comprises calculating a first standard deviation for at least a portion (or first portion)

of the pulse oximeter waveform data. At block 530, the process flow comprises interpolating a second standard deviation for at least a second portion of the pulse oximeter waveform data (different from the first portion of the pulse oximeter waveform data). At block 540, the process flow comprises determining the PVI based on the first standard deviation and the second standard deviation.

Figure 3:
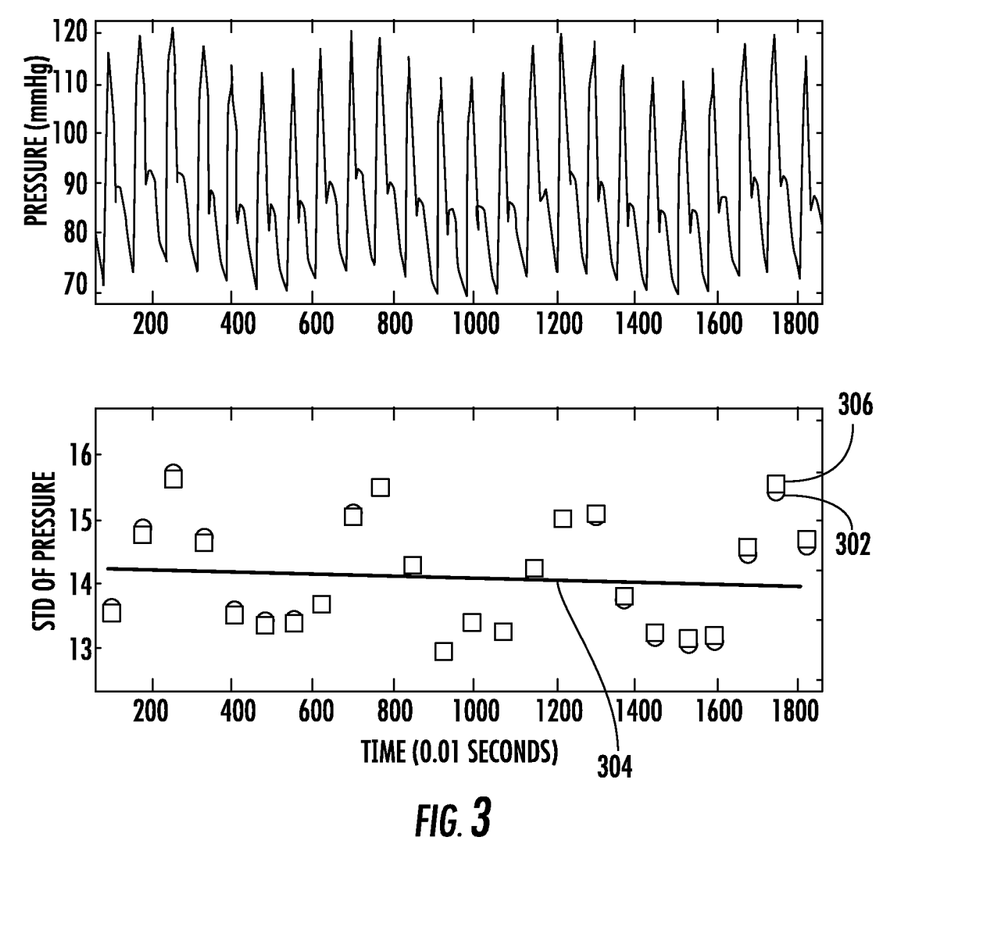
FIG. 3 shows an example of a hemodynamic parameter determination method using the pressure obtained before the bolus of phenylephrine is given to a patient.

FIG. 3 shows an example of the second method using the pressure obtained before a bolus of phenylephrine is given to a patient. The SVV obtained with the first method and the second method are quite close, as expected, since in the second method, the variation of the stroke volume is mainly induced by the respiration effect.

The top plot in FIG. 3 illustrates blood pressure before a bolus phenylephrine is given to a patient. In the bottom plot of FIG. 3, each circle (e.g., circle 302) shows the original standard deviation of blood pressure of each beat. The line 304 shows the fitted first order polynomial. Each square (e.g., square 306) shows the new standard deviation of blood pressure of each beat, obtained by subtracting the line 304 from the original standard deviation. Some circles are only partially visible or not visible because they at least partially overlap with some squares. The SVV calculated via the first and second methods are very close to each other. They are 17.03% and 17.04%, respectively.

Figure 4:
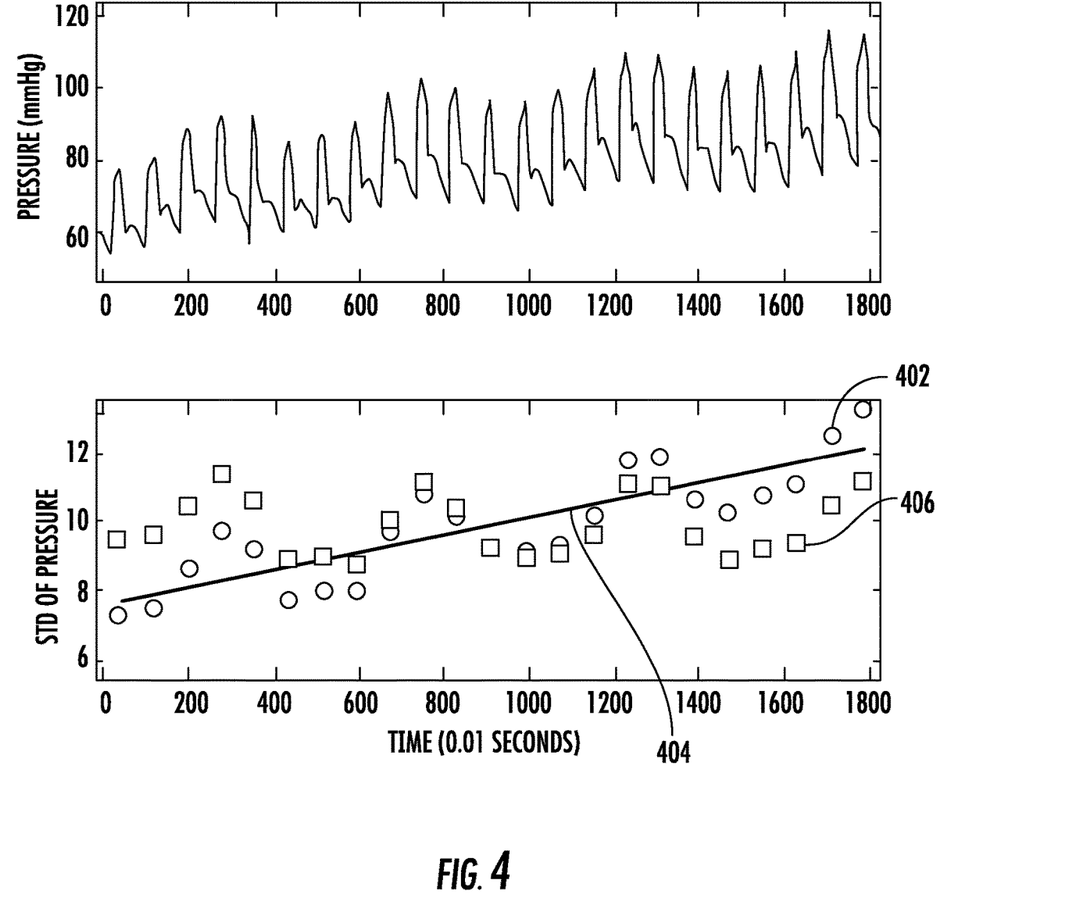
FIG. 4 shows an example of a hemodynamic parameter determination method using the pressure obtained after the bolus of phenylephrine is given to a patient.

FIG. 4 shows an example of the second method using the pressure obtained after the bolus of phenylephrine is given to a patient. The SVV obtained with the first method and the second method are quite different, as expected, since in the second method, the variation of the stroke volume is induced not only by the respiration effect, but also by other non-respiration induced effect. The SVV calculated using the second method removes much of the non-respiration effect and its value is much closer to the true value.

The top plot in FIG. 4 shows the blood pressure after a bolus phenylephrine is given to a patient. In the bottom plot of FIG. 4, each circle (e.g., circle 402) shows the original standard deviation of blood pressure of each beat. The line 404 shows the fitted first order polynomial. The square (e.g., square 406) shows the new standard deviation of blood pressure of each beat, obtained by subtracting the line 404 from the original standard deviation. Some circles are only partially visible or not visible because they at least partially overlap with some squares. The SVV calculated via the first and second methods are quite different. They are 44% and 24%, respectively.

The first order polynomial fit in the second method can be replaced with other orders of polynomial fit, such as the 2nd order, the 3rd order, etc., or can also be replaced with combinations of orders of polynomial fit. The fit does not have to use all data points; instead, it can be among selected data points, such as the first several data points and/or the last several data points.

Figure 6:
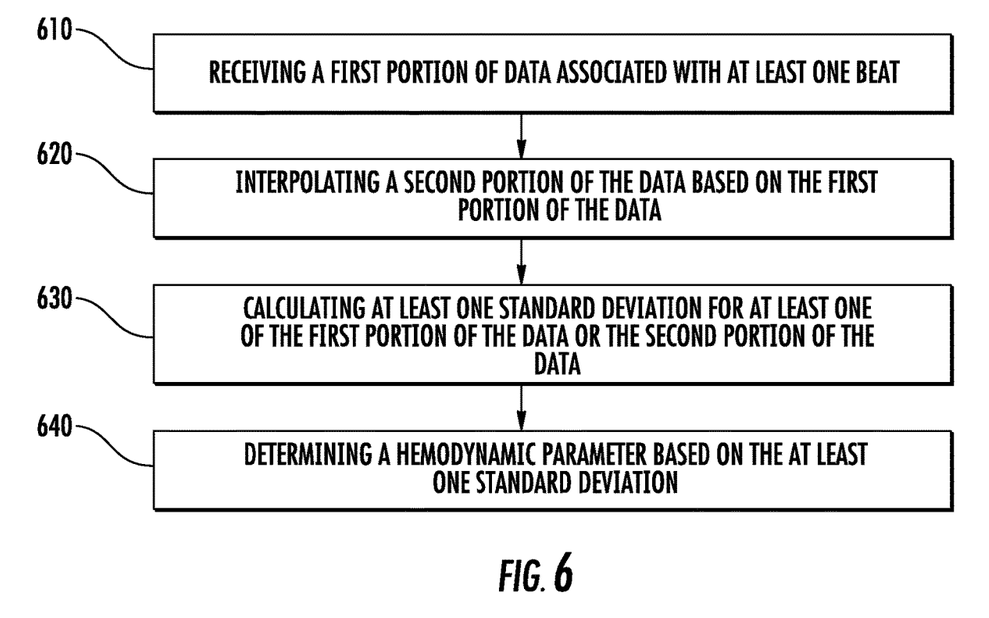
FIG. 6 shows another exemplary method for determining a hemodynamic parameter.

Referring now to FIG. 6, FIG. 6 presents another exemplary process flow for determining a hemodynamic parameter. At block 610, the process flow comprises receiving a first portion of data associated with at least one heart beat. At block 620, the process flow comprises interpolating a second portion of the data based on the first portion of the data. At block 630, the process flow comprises calculating at least one standard deviation for at least one of the first portion of the data or the second portion of the data. At block 640, the process flow comprises determining the hemodynamic parameter based on the at least one standard deviation. Each step of any process flow described herein may be performed by a single computing device processor or different computing device processors. In some embodiments, some of the steps may be performed by a single computing device processor, while other steps may be performed by individual computing device processors. Similar to FIG. 5, the process flow in FIG. 6 may be applicable to any hemodynamic parameter, including, but not limited to SVV, SPV, PPV, and PVI.

Figure 7:
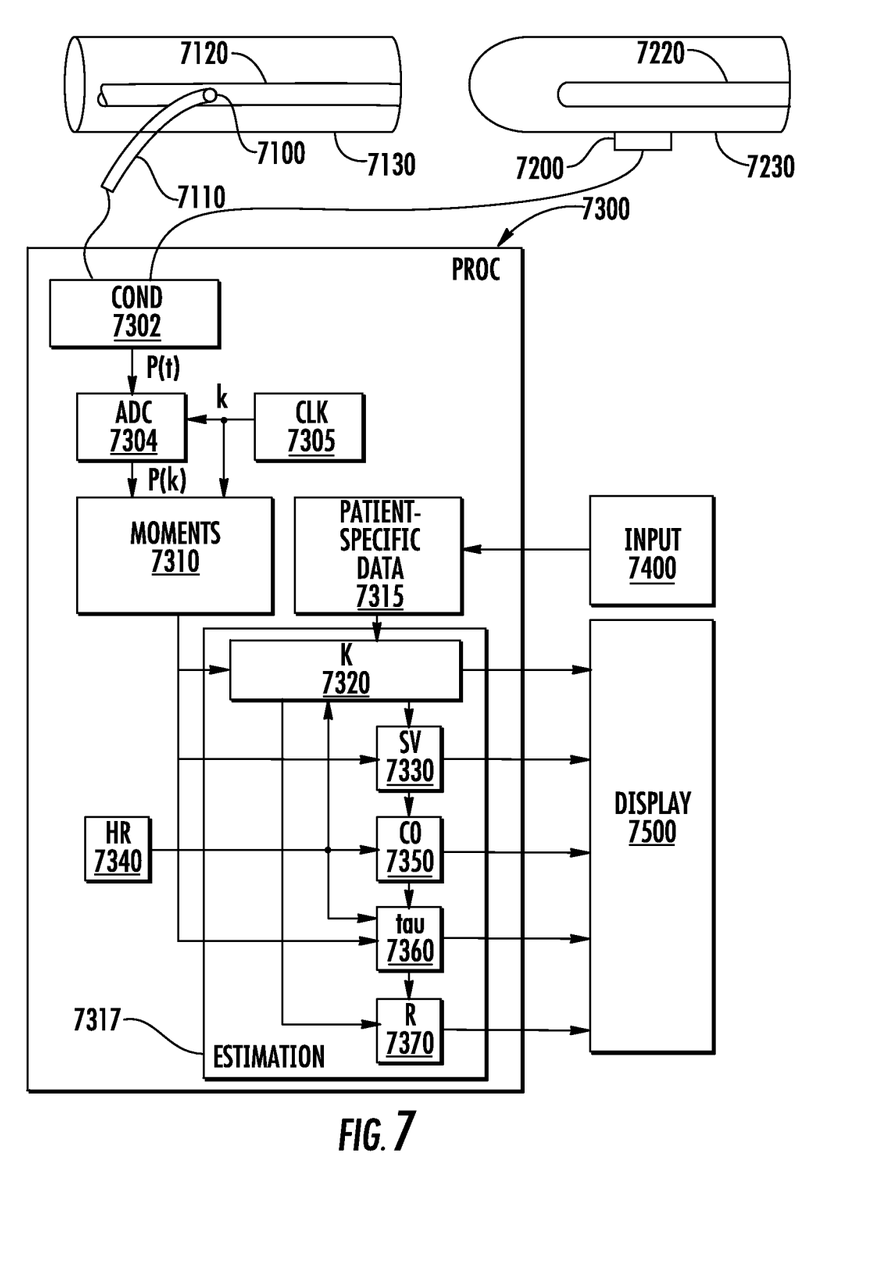
FIG. 7 shows an exemplary apparatus for determining a hemodynamic parameter.

Referring now to FIG. 7, FIG. 7 shows a system that may be used to determine any hemodynamic parameter, including, but not limited to SVV, SPV, PPV, and PVI. FIG. 7 shows two types of pressure sensing for the sake of conciseness; in most practical applications of the disclosure, either one or several variations will typically be implemented. In invasive applications of the disclosure, a conventional pressure sensor 7100 (e.g., a disposable pressure transducer) is mounted on a catheter 7110, which is inserted in an artery 7120 of a portion 7130 of the body of a human or animal patient. Such an artery could be an ascending aorta, or pulmonary artery, or, in order to reduce the level of invasiveness, the artery 7120 could be peripheral, such as the femoral, radial or brachial artery. In the non-invasive applications of the disclosure, a conventional pressure sensor 7200, such as a photo-plethysmographic blood pressure probe, is mounted externally in any conventional manner, for example using a cuff around a finger 7230 or a transducer mounted on the wrist of the patient. In some embodiments, the sensor 7100 or 7200 may comprise a pressure transducer (e.g., a disposable pressure transducer DPT). FIG. 7 schematically shows both types.

The signals from the sensors 7100, 7200 are passed via any known connectors as inputs to a processing system 7300, which includes one or more processors and other supporting hardware and system software (not shown) usually included to process signals and execute code. The disclosure may be implemented using a modified, standard, personal computer, or it may be incorporated into a larger, specialized monitoring system. In this disclosure, the processing system 7300 also may include, or is connected to, conditioning circuitry 7302 which performs such normal signal processing tasks as amplification, filtering, ranging, etc., as needed, as well as optional high pass filtering. The conditioned, sensed input pressure signal P(t) is then converted to digital form by a conventional analog-to-digital converter ADC 7304, which has or takes its time reference from a clock circuit 7305. As is well understood, the sampling frequency of the ADC 7304 should be chosen with regard to the Nyquist criterion so as to avoid aliasing of the pressure signal. The output from the ADC 7304 will be the discrete pressure signal P(k), whose values may be stored in conventional memory circuitry (not shown).

The values P(k) are passed to (usually, accessed from memory by) to a software module 7310 comprising computer-executable code for computing whichever of the parameters are to be used in the chosen algorithm for calculating the K.

The patient-specific data such as age, height, weight, body surface area, etc., is stored in a memory 7315, which may also store other predetermined parameters. These values may be entered using any known input device 7400 in the conventional manner.

A compliance calculation module 7320, also comprising computer-executable code, then takes as inputs the various moment and patient-specific values and performs the chosen calculations for computing the arterial compliance function K (or compliance factor C). For example, the module 7320 could enter the parameters into the expression given below for K (or C), or into some other expression derived by creating an approximating function that best fits a set of test data. The calculation module 7320 preferably also selects the time window over which each K, C, SV, CO, SVV, SPV, PPV, and/or PVI estimate is generated. This may be done as simply as choosing which and how many of the stored, consecutive, discretized P(t) values P(k) are used in each calculation, which is the same as selecting n in the range k=0, . . . , (n−1).

Taking K (and other parameters such as C) as inputs, a stroke volume computation module 7330, again comprising computer-executable code, then computes an SV estimate. Taking as inputs both SV and a heart rate value HR generated by any known hardware device 7340 or software routine (for example, using Fourier or derivative analysis) for measuring heart rate along with any other parameters described herein, a CO computation module 7330 may then generate an estimate of CO using the method described herein.

Additional software modules 7360 and 7370 may be included to perform the calculations described above to estimate the exponential pressure decay constant tau and vascular resistance R. As used herein, the vascular resistance R may also be referred to as the systemic vascular resistance. Still additional software modules (not shown) may be included to determine or calculate any hemodynamic parameter described herein, including, but not limited to, SVV, PPV, SPV, or PVI.

As shown in FIG. 7, the software modules 7320, 7330, 7350, 7360, and 7370, that is, whichever of these are included, may be implemented within an estimation software component 317, which may of course be combined with the moment-calculating component 7310, or with other software components of the processing system 7300 as desired.

It is not necessary for the system to compute SV or CO if these values are not of interest. The same is true for tau and R. In such case, the corresponding software modules will of course not be needed and may be omitted. For example, the disclosure could be used in a study of arterial compliance itself. Nonetheless, as FIG. 7 illustrates, any or all of the results K, SV, CO, tau and R may be passed to any conventional display or recording device 7500 for presentation to and interpretation by a user or another system. As with the input device 7400, the display 7500 will typically be the same as is used by the processing system for other purposes.

The disclosure further relates to a computer program loadable in a computer unit or the processing system 7300 in order to execute the methods of the disclosure. Moreover, the various software modules 7310, 7315, 7320, 7330, 7340, 7350, 7360, and 7370 used to perform the various calculations and perform related method steps according to the disclosure may also be stored as computer-executable instructions on a computer-readable medium in order to allow the instructions to be loaded into and executed by different processing systems.

In accordance with embodiments of the disclosure, the term "module" with respect to an apparatus may refer to a hardware component of the apparatus, a software component of the apparatus, or a component of the apparatus that includes both hardware and software. As used herein, a module may include one or more modules, where each module may reside in separate pieces of hardware or software. As used herein, an apparatus may alternatively be referred to as a "system" or a "device."

Although many embodiments of the present disclosure have just been described above, the present disclosure may be embodied in many different forms and should not be construed as limited to the embodiments set forth herein; rather, these embodiments are provided so that this disclosure will satisfy applicable legal requirements. Also, it will be understood that, where possible, any of the advantages, features, functions, devices, and/or operational aspects of any of the embodiments of the present disclosure described and/or contemplated herein may be included in any of the other embodiments of the present disclosure described and/or contemplated herein, and/or vice versa. In addition, where possible, any terms expressed in the singular form herein are meant to also include the plural form and/or vice versa, unless explicitly stated otherwise. Accordingly, the terms "a" and/or "an" shall mean "one or more," even though the phrase "one or more" is also used herein. Like numbers refer to like elements throughout.

As will be appreciated by one of ordinary skill in the art in view of this disclosure, the present disclosure may include and/or be embodied as an apparatus (including, for example, a system, apparatus, machine, device, computer program product, and/or the like), as a method (including, for example, a business method, computer-implemented process, and/or the like), or as any combination of the foregoing. Accordingly, embodiments of the present disclosure may take the form of an entirely business method embodiment, an entirely software embodiment (including firmware, resident software, micro-code, stored procedures in a database, or the like), an entirely hardware embodiment, or an embodiment combining business method, software, and hardware aspects that may generally be referred to herein as a "system" or "apparatus." Furthermore, embodiments of the present disclosure may take the form of a computer program product that includes a computer-readable storage medium having one or more computer-executable program code portions stored therein. As used herein, a processor, which may include one or more processors, may be "configured to" perform a certain function in a variety of ways, including, for example, by having one or more general-purpose circuits perform the function by executing one or more computer-executable program code portions embodied in a computer-readable medium, and/or by having one or more application-specific circuits perform the function.

It will be understood that any suitable computer-readable medium may be utilized. The computer-readable medium may include, but is not limited to, a non-transitory computer-readable medium, such as a tangible electronic, magnetic, optical, electromagnetic, infrared, and/or semiconductor system, device, and/or other apparatus. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present disclosure, however, the computer-readable medium may be transitory, such as, for example, a propagation signal including computer-executable program code portions embodied therein.

One or more computer-executable program code portions for carrying out operations of the present disclosure may include object-oriented, scripted, and/or unscripted programming languages, such as, for example, Java, Perl, Smalltalk, C++, SAS, SQL, Python, Objective C, JavaScript, and/or the like. In some embodiments, the one or more computer-executable program code portions for carrying out operations of embodiments of the present disclosure are written in conventional procedural programming languages, such as the "C" programming languages and/or similar programming languages. The computer program code may alternatively or additionally be written in one or more multi-paradigm programming languages, such as, for example, F #.

Some embodiments of the present disclosure are described herein with reference to flowchart illustrations and/or block diagrams of apparatus and/or methods. It will be understood that each block included in the flowchart illustrations and/or block diagrams, and/or combinations of blocks included in the flowchart illustrations and/or block diagrams, may be implemented by one or more computer-executable program code portions. These one or more computer-executable program code portions may be provided to a processor of a general purpose computer, special purpose computer, and/or some other programmable data processing apparatus in order to produce a particular machine, such that the one or more computer-executable program code portions, which execute via the processor of the computer and/or other programmable data processing apparatus, create mechanisms for implementing the steps and/or functions represented by the flowchart(s) and/or block diagram block(s).

The one or more computer-executable program code portions may be stored in a transitory and/or non-transitory computer-readable medium (e.g., a memory or the like) that can direct, instruct, and/or cause a computer and/or other programmable data processing apparatus to function in a particular manner, such that the computer-executable program code portions stored in the computer-readable medium produce an article of manufacture including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with, and/or replaced with, operator- and/or human-implemented steps in order to carry out an embodiment of the present disclosure.

While certain exemplary embodiments have been described and shown in the accompanying drawings, it is to be understood that such embodiments are merely illustrative of and not restrictive on the broad disclosure, and that this disclosure not be limited to the specific constructions and arrangements shown and described, since various other changes, combinations, omissions, modifications and substitutions, in addition to those set forth in the above paragraphs, are possible. Those skilled in the art will appreciate that various adaptations, modifications, and combinations of the just described embodiments can be configured without departing from the scope and spirit of the disclosure. Therefore, it is to be understood that, within the scope of the appended claims, the disclosure may be practiced other than as specifically described herein.

What is claimed is:

1. A method for determining a hemodynamic parameter, the method comprising:
    receiving data associated with at least one heart beat;
    calculating a first standard deviation for at least a portion of the data;
    determining, using a computing device processor, a polynomial function that fits the first standard deviation, the polynomial function being associated with at least one polynomial coefficient;
    interpolating a second standard deviation for at least a second portion of the data, wherein the second standard deviation is interpolated by subtracting the polynomial function from the first standard deviation; and
    determining, using the computing device processor, the hemodynamic parameter based on multiplying a constant and a standard deviation of the second standard deviation to produce a first computation, and dividing the first computation by a mean of the first standard deviation.

2. The method of claim 1, wherein the hemodynamic parameter comprises a stroke volume variation, and wherein the data comprises blood pressure data.

3. The method of claim 1, wherein the hemodynamic parameter comprises a pulse pressure variation, and wherein the data comprises pulse pressure data.

4. The method of claim 1, wherein the hemodynamic parameter comprises a systolic pressure variation, and wherein the data comprises systolic pressure data.

5. The method of claim 1, wherein the hemodynamic parameter comprises a plethysmographic variability index, and wherein the data comprises pulse oximeter waveform data.

6. The method of claim 1, wherein the polynomial function is based on a least-squares function.

7. The method of claim 1, wherein receiving data comprises measuring at least one arterial blood pressure waveform and identifying the at least one heart beat.

8. The method of claim 1, further comprising subtracting the second standard deviation from the first standard deviation.

9. The method of claim 1, wherein the polynomial function is a first order polynomial function.

10. The method of claim 1, wherein the polynomial function is an $n^{th}$ order polynomial function.

11. An apparatus for determining a hemodynamic parameter, the apparatus comprising:
    a communication interface;
    a memory;
    a processor; and
    a module stored in the memory, executable by the processor, and configured to:
        receive data associated with at least one heart beat;
        calculate a first standard deviation for at least a portion of the data;
        determine a polynomial function that fits the first standard deviation, the polynomial function being associated with at least one polynomial coefficient;
        interpolate a second standard deviation for at least a second portion of the data, wherein the second standard deviation is interpolated by subtracting the polynomial function from the first standard deviation; and
        determine the hemodynamic parameter based on multiplying a constant and a standard deviation of the second standard deviation to produce a first computation, and dividing the first computation by a mean of the first standard deviation.

12. The apparatus of claim 11, wherein the hemodynamic parameter comprises a stroke volume variation, and wherein the data comprises blood pressure data.

13. The apparatus of claim 11, wherein the hemodynamic parameter comprises a pulse pressure variation, and wherein the data comprises pulse pressure data.

14. The apparatus of claim 11, wherein the hemodynamic parameter comprises a systolic pressure variation, and wherein the data comprises systolic pressure data.

15. The apparatus of claim 11, wherein the hemodynamic parameter comprises a plethysmographic variability index, and wherein the data comprises pulse oximeter waveform data.

16. The apparatus of claim 11, wherein the polynomial function is based on a least-squares function.

17. The apparatus of claim 11, wherein the data associated with the at least one heart beat is measured from at least one arterial blood pressure waveform, and wherein the apparatus is further configured to identify the at least one heart beat from the received data.

18. The apparatus of claim 11, wherein the apparatus is further configured to subtract the second standard deviation from the first standard deviation.

19. The apparatus of claim 11, wherein the polynomial function is a first order polynomial function.

20. The apparatus of claim 11, wherein the polynomial function is an $n^{th}$ order polynomial function.

\* \* \* \* \*